United States Patent [19]

Jones

[11] Patent Number: 5,661,310

[45] Date of Patent: Aug. 26, 1997

[54] RADIATION DOSE MAPPING SYSTEMS AND METHODS

[75] Inventor: Scott C. Jones, Solon, Ohio

[73] Assignee: Keithley Instruments, Inc., Cleveland, Ohio

[21] Appl. No.: 682,680

[22] PCT Filed: Mar. 27, 1995

[86] PCT No.: PCT/US95/03748

§ 371 Date: Sep. 24, 1996

§ 102(e) Date: Sep. 24, 1996

[87] PCT Pub. No.: WO95/26513

PCT Pub. Date: Oct. 5, 1995

Related U.S. Application Data

[63] Continuation of Ser. No. 218,362, Mar. 28, 1994, abandoned.

[51] Int. Cl.⁶ .................. G01T 1/105; G01T 1/115
[52] U.S. Cl. .................. 250/584; 250/337; 250/580
[58] Field of Search .................. 250/337, 484.3, 250/580, 584, 585, 586

[56] References Cited

U.S. PATENT DOCUMENTS

| | | |
|---|---|---|
| 3,975,637 | 8/1976 | Ikedo et al. . |
| 4,091,284 | 5/1978 | Yamamoto et al. . |
| 4,204,119 | 5/1980 | Yasuno et al. .................. 250/337 |
| 4,481,416 | 11/1984 | Rabatin . |
| 4,507,562 | 3/1985 | Gasiot et al. . |
| 4,849,639 | 7/1989 | Born et al. . |
| 4,878,234 | 10/1989 | Pfeiffer et al. . |
| 5,083,031 | 1/1992 | Hoelsher et al. . |
| 5,391,879 | 2/1995 | Tran et al. . |
| 5,430,308 | 7/1995 | Feichtner et al. .................. 250/580 |
| 5,508,523 | 4/1996 | Tawil et al. .................. 250/337 |

FOREIGN PATENT DOCUMENTS

| | | |
|---|---|---|
| 2483117 | 11/1981 | France . |
| 58-143284 | 8/1983 | Japan . |
| 61-153578 | 12/1984 | Japan . |

OTHER PUBLICATIONS

"Charge–Coupled Devices for Quantitative Electronic Imaging", Photometrics, Ltd., Tucson, AZ (Aug. 1992).

Yamamoto et. al., "Sptial Distribution Readout System of Thermoluminescence Sheets II", Nuc. Instr. and Meth. in Physics Research, A(256), 1987, pp. 567–575.

Braunlich, Peter F., "Laser Heated Thermoluminescense Dosimetry", Nova Science Publishers, inc., Commack, NY (1992).

Braunlich, Peter F., "Present State and Future of TLD Laser Heating", Nuclear Technlogy Publishing, (1990).

*Primary Examiner*—Carolyn E. Fields
*Assistant Examiner*—Edward J. Glick
*Attorney, Agent, or Firm*—Wells, St. John, Roberts, Gregory & Matkin, P.S.

[57] ABSTRACT

A dose distribution analyzer (20) and methods for providing a radiation dose map indicating energy of a spacially variable radiation pattern beamed onto a dose map radiation dosimeter (10). The radiation dosimeter (10) is exposed to a proposed spacially variable radiation pattern such as used in a phantom patient for patient radiation dose treatment verification. The dosimeter (10) is subsequently analyzed by the dose distribution analyzer (20). Such analyzer includes a phosphor stimulator (53), an image forming subsystem (38), and an image sensor (37). A dosimeter holder (32) holds the dosimeter near the phosphor stimulator (53). A system controller (22) is connected to receive image data from the image sensor (37) while the dosimeter (10) is stimulated. The controller (22) utilizes the image data to derive a radiation dose map which indicates the distribution of radiation in the spacially variable radiation pattern which strikes the dosimeter (10).

12 Claims, 3 Drawing Sheets

RADIATION DOSE MAPPING SYSTEMS AND METHODS

This is a National Stage Application filed under 35 U.S.C. §371 of PCT/US 95/03748, filed 27 Mar. 1995, which is a continuation of U.S. patent appliction Ser. No. 08/218,362, filed 28 Mar. 1994, now abandoned.

1. Technical Field

This invention relates to dose mapping of spacially variable radiation patterns, particularly of radiation patterns as are used in medical radiation treatment.

2. Background Art

Radiation therapy is used in the treatment of various medical conditions. In many cases such radiation treatments seek to apply a relatively greater dose of radiation at some specific location, for example, to a cancerous tumor located in a position within the human body. Therefore, it is usually necessary, prior to actual patient treatment, to design a radiation exposure plan or design which uses one or more radiation beams of varying shape, size, strength, intensity, convergence, orientation or duration. Such exposure plans can direct the various beam or beams at the specific region of tissue which is to be treated, while minimizing the radiation dose beamed to adjacent tissues. Avoiding radiation exposure of adjacent tissues becomes especially important where the tissues being treated are adjacent to tissues which are particularly sensitive to radiation injury, such as adjacent to optic nerves, brain tissues, and other tissues.

In an effort to minimize the radiation damage to surrounding tissues, the medical profession uses simulated human models; typically called phantoms. The phantoms are used to help devise and analyze proposed radiation dose plans prior to actual patient exposure. The phantoms are preferably three-dimensional models having dimensions similar to the person being treated. The materials used to make the phantoms are selected to simulate the radiation absorbance of the tissues of the body or body parts being modeled. This tissue-equivalency is important to good modeling and analysis. Despite using a great degree of care, the determination of radiation doses is a difficult science and requires interpretive and predictive judgment by the practicing radiologist.

Prior art radiation treatment dose mapping systems have utilized radiation sensitive photographic films such as X-ray films, which are positioned at appropriate locations within a phantom during administration of proposed radiation doses. Such films must be developed using relatively time consuming chemical procedures. This slows the treatment planning process and reduces the number of tests and the precision of treatment designs which might otherwise be obtained.

An alternative approach has been to utilize one or more discrete radiation intensity probes during test dose administration. This approach suffers from not providing two-dimensional or three-dimensional maps of radiation exposure over the areas or spaces of a phantom patient. A continuous distribution mapping is highly desirable in order to precisely identify spacial coordinates of radiation peaks and to more efficiently fine tune or adjust radiation sources to achieve desired dose concentrations at the desired spatial coordinates relative to the phantom and patient.

The invention described below provides a system for improved mapping of spacially variable radiation patterns such as used in medical radiation treatment. The apparatus and methods of the invention may find additional application in such fields as mapping of accelerator beam profiles and mapping of radiation patterns used to test electronic circuits and other devices for radiation hardness. The invention provides the advantages of substantially continuous field mapping, to provide dose images. Additionally, the dynamic range is improved in most instances as compared to prior technologies. The present invention may also help in eliminating other disadvantages of prior technologies. The apparatus and methods of the invention allow for high speed radiation dose mapping without the requirement of chemical processing while providing a dose image of good resolution and good dynamic range.

BRIEF DESCRIPTION OF THE DRAWINGS

One or more preferred forms of the invention are described herein with reference to the accompanying drawings. The drawings are briefly described below.

BEST MODES FOR CARRYING OUT THE INVENTION AND DISCLOSURE OF INVENTION

Figure 1:
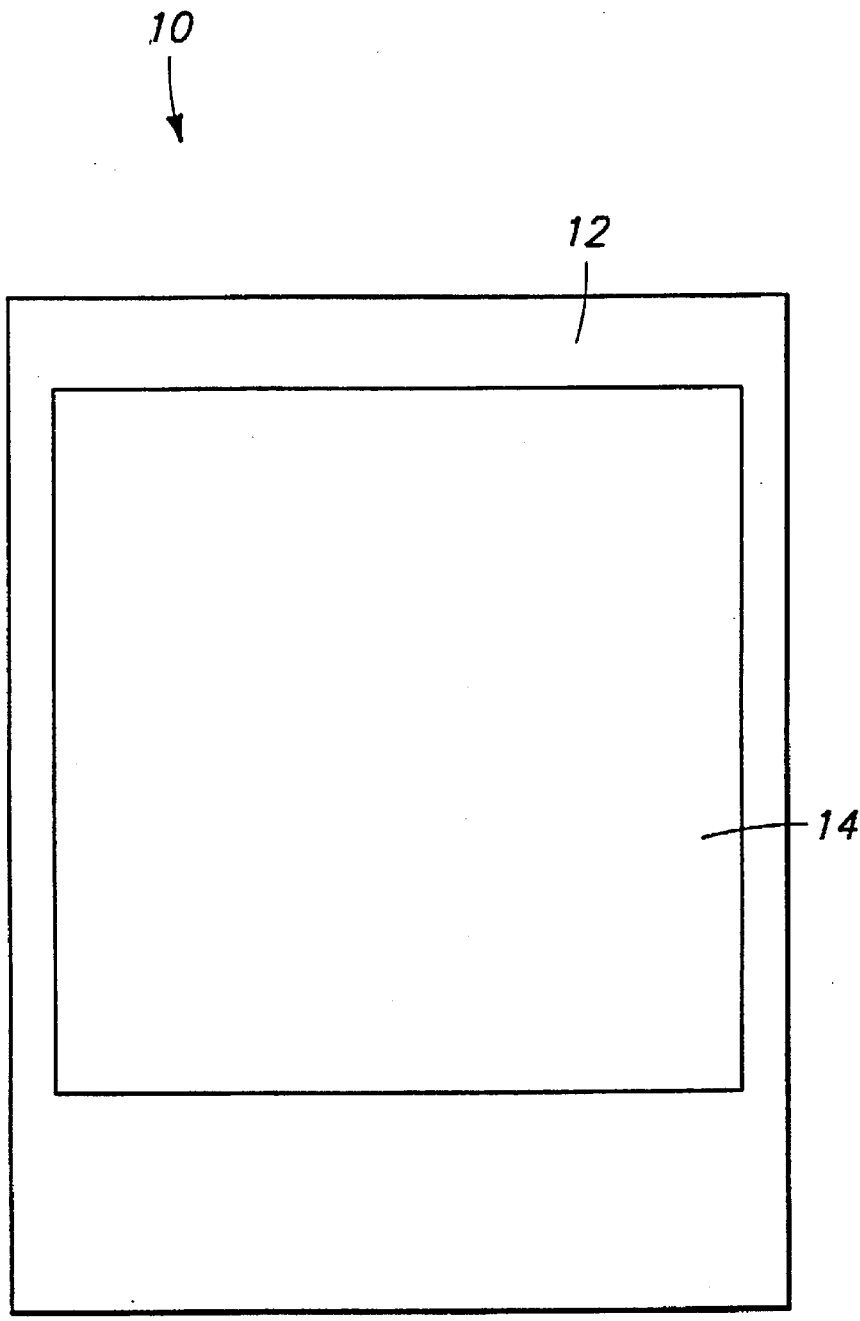
FIG. 1 is a front view of a dose map radiation dosimeter in accordance with a preferred embodiment of the invention.

FIG. 1 shows a dose map radiation dosimeter 10 in accordance with a preferred embodiment of the invention. Dosimeter 10 is intended to be used in a phantom patient for patient radiation dose treatment verification. Dosimeter 10 includes a thin substrate layer 12 which can be pliable, or a flat card or plate. Substrate layer(s) 12 can be of Kapton™ or other polyimide plastic, or other suitable material which is preferably nearly tissue-equivalent.

Dosimeter 10 also comprises a dosimeter layer 14 made of a suitable luminescent material or materials. Dosimeter layer 14 stores radiant energy and emits a transitory dosimeter luminescent image. The transitory dosimeter luminescent image has luminescent intensity which varies across the dose measurement area in relation to the amount of incident energy of a spacially variable radiation pattern previously beamed onto the dose map radiation dosimeter. Dosimeter 10 can also be made in accordance with the teachings of U.S. Pat. No. 5,083,031 which is hereby incorporated by reference.

Preferable luminescent materials are referred to as "dosimetric phosphors." Incident radiation alters the energy states of the atoms of such phosphors, making the phosphors capable of storing dose information relating to the incident radiation. After exposure to such radiation, the phosphors can be stimulated to luminesce at an intensity which relates to the energy of the previously-applied radiation. $CaSO_4$:Dy, $MgB_4O_7$:Dy, and LiF:Ti,Mg are examples of phosphors which are stimulable by heat to luminesce in relation to the energy of previously-applied radiation. Other dosimetric phosphors, such as MgS:Eu, MgS:Sm, CaS:Ce, BaFCl:Eu, and $CaSO_4$:Sm are stimulated by exposure to light.

In accordance with a preferred embodiment of the invention, one or more of these materials is applied to substrate layer 12 to form a sensing area or areas 14. The sensing area is preferably formed as a continuous or substantially continuous layer. The dosimeter can be produced using production processes as set out in detail in the patent incorporated by reference above. Measurement area 14 is most preferably rectangular and formed with dimensions of approximately two inches by two inches, although other sizes are possible.

Figure 2:
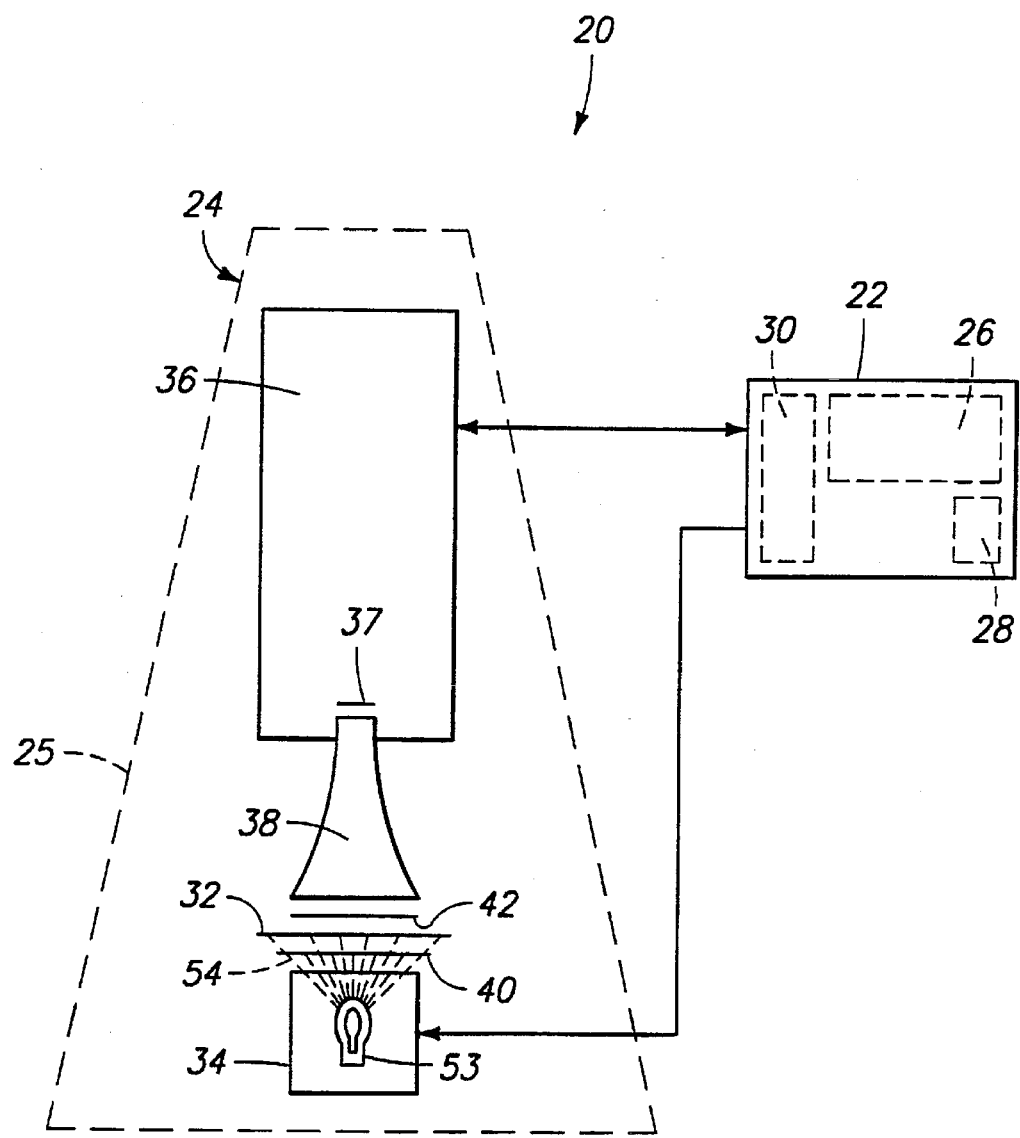
FIG. 2 is a diagrammatic representation of a dose distribution analyzer in accordance with a preferred embodiment of the invention.

FIG. 2 shows a preferred dose distribution analyzer 20 according to this invention. Analyzer 20 provides a radiation dose map indicating the energy of a spacially variable radiation pattern beamed onto a dose map radiation dosimeter, such as dosimeter 10 discussed above. Analyzer 20 includes a computer-based controller 22 and a stimulation and imaging apparatus 24. Controller 22 is a conventional desktop computer, including a data processor 26, a data store or memory 28, digital interface circuitry 30, and other components which are not specifically shown but which are common to widely-available desktop computers.

Stimulation and imaging apparatus 24 includes a dosimeter holder 32, a dosimeter stimulator 34, and an electronic camera 36. The components of this apparatus are preferably housed in a dark enclosure 25 to allow better detection of luminescing materials.

Dosimeter holder 32 is configured to hold dosimeter 10 by its edges in a horizontal orientation so that its surfaces are exposed along first and second faces from above and from below, respectively. Dosimeter stimulator 34 is positioned below holder 32 to direct heat or light, depending on the nature of phosphor used, onto the bottom surface of a dosimeter held within holder 32. Camera 36 is positioned above dosimeter holder 32 to produce an electronic representation of the light emissions produced by the dosimeter.

In the preferred embodiment, stimulator 34 comprises an infrared light source for beaming an infrared stimulation beam onto the bottom side of the radiation dosimeter. In this embodiment, phosphor stimulation is accomplished by exposure of the dose measurement area to light. Accordingly, the dosimeter must be fabricated with an appropriate stimulable dosimetric phosphor such as described above.

A quartz halogen incandescent lamp 53 is preferably used to provide the infrared stimulation beam 54. However, it is further advantageous to utilize only a narrow band of the infrared spectrum to stimulate the dosimetric phosphors of the dosimeter. An optical stimulator source filter 40 is therefore provided in the infrared light source, or between it and dosimeter holder 32, to produce such a narrow-band infrared spectrum. In addition, an optical image filter 42 is positioned between stimulator 34 and image sensor 37 to prevent the light produced by stimulator 34 from being conveyed to camera 36, and from affecting sensed luminescence intensity.

Figure 3:
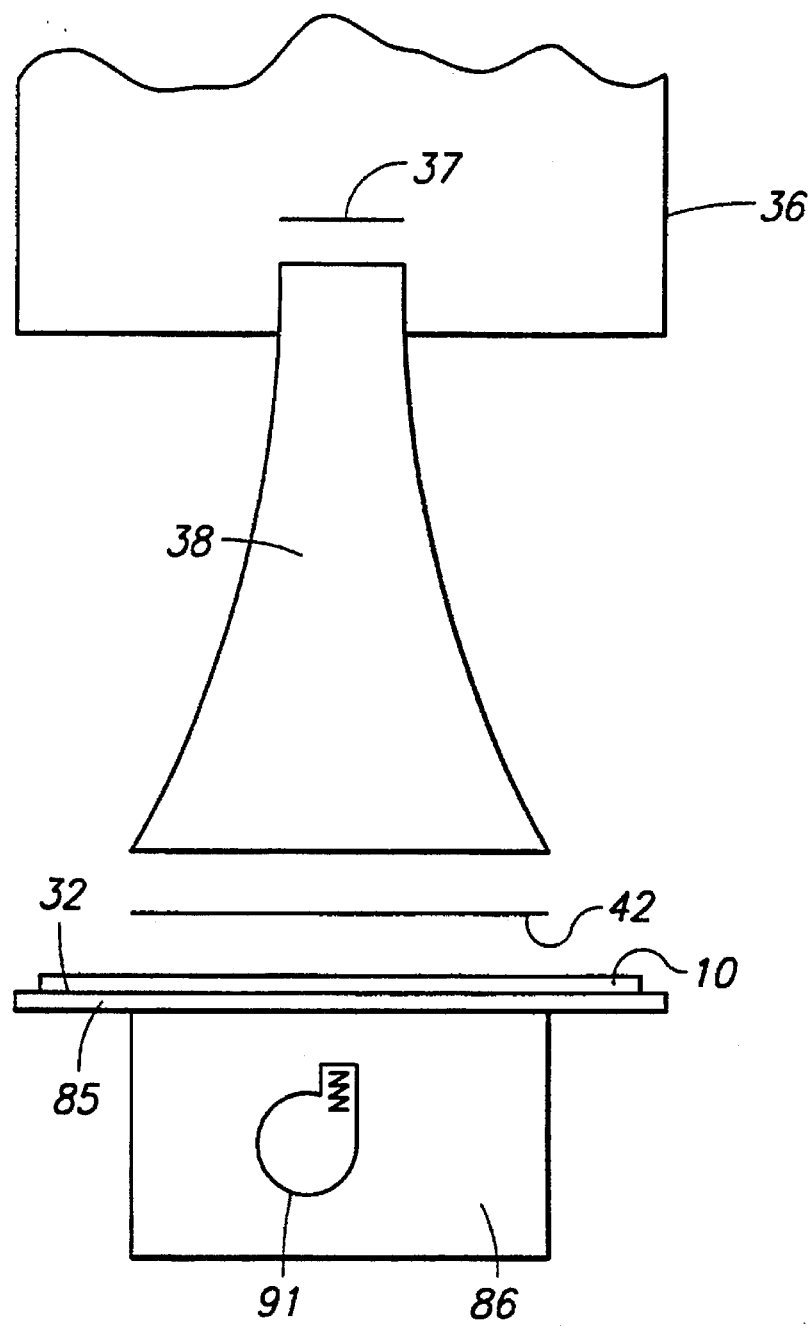
FIG. 3 is a diagrammatic representation showing an alternative heat stimulation subsystem used in a dose distribution analyzer.

FIG. 3 shows that the dosimeter stimulator may alternatively comprise a heat source 86 positioned for heating a dose map radiation dosimeter held in dosimeter holder 32. Such a heat source would be used in conjunction with a dosimeter having heat-stimulable phosphors. Such a heat source might comprise a quartz-tungsten halogen lamp, or as shown, an electrically heated gas blower 91 positioned to impinge heated gas directly upon the dosimeter or upon a heat distribution piece 85. Alternatively, the heat source might comprise a thermally conductive heat distribution plate 85. Heat distributor 85 can be provided with a suitable heat source, such as an electric resistance element (not shown). Heat distributor 85 is positioned directly beneath the dosimeter holder in contact with the dosimeter when installed. Heat distributor 85 serves to distribute heat evenly across the dosimeter's measurement area.

Camera 36 includes an image sensor 37. Image sensor 37 is a photosensitive device which is capable of sensing and resolving the intensity of luminescence in a transitory dosimeter luminescent image which is taken from a luminescent discharge emitted from dosimeter 10 upon stimulation. In the preferred embodiment, image sensor 37 is an electronic imager or imaging array such as a charge-coupled device (CCD) array. The image sensor preferably has a plurality of individual photosensitive elements arranged in a rectangular planar two-dimensional array or matrix. The preferred image sensor has a digital output signal having a wide dynamic range, e.g., approximately 20 decibels or greater; more preferably 40 decibels or greater.

Camera 36 also includes a suitable imaging subsystem for taking a luminescent discharge from a dosimeter held in holder 32 and forming an image thereof onto image sensor 37. FIG. 2 shows a preferred image forming construction including an image forming device 38 positioned to receive an image of the transitory dosimeter luminescent discharge emitted from a dosimeter. As shown, image forming device 38 includes an image transferring device which can closely be positioned to both the dosimeter holder 32 and the image sensor 37. This allows much of the luminescent discharge from a dosimeter held in holder 32 to be transferred to the image sensor 37 thus improving emission collection and sensitivity of the overall system.

In the preferred embodiment, image formation device 38 includes as a principal part a bundle of coherent optical fibers positioned to extend from near or immediately adjacent one surface of the dose map radiation dosimeter to near or immediately adjacent image sensor 37. Such an optical fiber bundle conveys most or all of the dosimeter luminescent image to sensor 37. The optical fiber bundle is preferably tapered, with each fiber decreasing in diameter from the dosimeter to the imaging sensor. Such a tapered optical fiber bundle reduces the size of the transitory dosimeter luminescent discharge image conveyed to the image sensor. Image size reduction is desired to: convey maximum amounts of discharged light or other emissions; transfer such emissions with minimal loss to the image sensor; and demagnify the discharge image and bring it into size with the image sensor. The image formation and transfer device 38 preferably uses an optical fiber bundle having sufficient numbers of individual optical fibers so as to correspond to the resolution needed in the image sensor to provide the desired overall resolution of the resulting dose map. In a preferred embodiment, the optical fiber bundle uses optical fibers having a large end with diameters of approximately 20–100 microns which correspond to diameters of 10–50 microns at the output end of the fibers near image sensor 37. This roughly corresponds to the spacial resolution of a CCD image sensor.

The image forming subsystem 38 also preferably includes suitable image adjustment mechanisms for improving the collection and transfer of luminescent discharge from a dosimeter held in holder 32 to the image sensor 37. This is advantageously in the form of an input adjustment mechanism (not shown) for adjusting the relative spacing between the input end of the optical fibers and the surface of a dosimeter held in dosimeter holder 32. Image adjustment can also be provided in the form of an output adjustment mechanism (not shown) which allows adjustment of the relative position between the output end of the optical fibers and image sensor 37. However, it is preferred that the image sensor and fiber bundle be directly coupled without adjustment.

Image formation device 38 may in a less preferred alternative embodiment comprise an optical lens, such as a commercially-available camera lens (not shown), positioned appropriately between dosimeter holder 32 and image sensor 37 to focus a reduced-size image of a luminescing dosimeter surface onto image sensor 37. An optical lens, however, results in an inefficient collection of luminescent emission, and is therefore less preferred than the optical fiber bundle.

Image formation device 38 transmits the luminescent discharge from a dosimeter to the image sensor. This is preferably done by transferring or conveying individual regions or areas of a dosimeter's dose measurement area to individual elements or pixels of image sensor 37. The individual sensory elements of the CCD or other image sensor are sensitive to the intensity of the luminescent discharge to provide electronic image information or data indicating the varying intensity of the transitory dosimeter luminescent discharge image across the two-dimensional surface of the dosimeter dose measurement area. As a result, camera 36 produces a plurality of intensity values, each of which is generated by a pixel of the sensor 37 and which represents the luminescent intensity of a specific region of the dose measurement area. This information is transferred to computer 22 and stored in data storage 28. Combined, the numerous intensity values provide a map of varying luminescent intensity over substantially the entire dose measurement area. Since the dose measurement area of the dosimeter is preferably continuous, the resulting dose image information provides an effectively continuous dose map representation of the sufficiently energetic radiant energy received by the dosimeter during exposure to stimulating radiation.

The invention also includes novel methods. The novel methods include selecting a suitable dosimeter. The preferred dosimeters are dose map radiation dosimeters, such as described above. The preferred dosimeters are selected according to the intended use to have a dosimeter sensory area or layer which stores energy as a function dependent upon the energy of the radiation to which the dosimeter will be exposed. Examples of suitable phosphors for use in the dosimeter sensing layers, such as 14, are explained hereinabove. The selected dosimeters are most preferably provided with a dosimeter layer which is a continuous or substantially continuous luminescent phosphor.

Such methods also preferably include the method step of exposing the selected dose map radiation dosimeter. Such exposing is performed by generating a radiation field having sufficiently energetic radiation so as to cause ionization or other activation of the dosimeter sensing layer. The ionizing radiation causes storage of radiant energy in the dosimeter sensing layer. The radiation field is typically of variable intensity to provide a beamed radiation pattern which produces a dosimeter-incident radiation pattern which is spacially variable.

Such exposing step is advantageously performed by positioning the dose map radiation dosimeter in a monitoring location for exposure to a radiation field to be determined. Such positioning can be done to a monitoring position within a phantom patient at a location where radiation dose strength is to be determined. The dosimeter is left in the monitoring location while a proposed radiation exposure plan is effected. The radiation field is effected by generating the radiation field and beaming a desired radiation pattern onto the phantom patient and onto the measurement area 14 of the dosimeter.

The methods also advantageously include removing the dose map radiation dosimeter from the phantom patient or other monitoring location. This is done as appropriate for the phantom or other location used.

The removed dosimeter is then preferably used by reading the dose map information contained therein. This reading operation most preferably includes positioning the dosimeter for stimulation, such as positioning the dosimeter in dosimeter holder 32. In this positioning step the dosimeter is accessible to a stimulating beam or to a heat source.

A subsequent methodical step of the invention includes stimulating the dose measurement area of the dosimeter, causing it to emit a transitory luminescent discharge. In a preferred embodiment the dosimeter is approximately simultaneously stimulated with radiation as shown in FIG. 2. The stimulating step is preferably done by beaming a stimulating beam onto the sensing area of the previously exposed dose map radiation dosimeter. The stimulating beam can be of various types. A preferred stimulating beam is an infrared beam having a stimulating beam wavelength range or bandwidth which lies principally outside the range or bandwidth of the luminescent discharge which is emitted from the dosimeter sensing area. Thus the stimulating beam can be effectively filtered to reduce any effects associated with impingement of the stimulating beam upon the image sensor. The stimulated transitory luminescent discharge from dosimetric area 14 is typically a visible light emission or other suitable luminescent discharge emission. In general such emissions vary from point to point across the dosimeter sensing area.

The stimulating step can alternatively be accomplished by heating the dosimeter. This alternative approach is can be accomplished by impinging a flow of heated gas upon the dosimeter sensing area or the entire dosimeter. The heating step can also be accomplished by contacting the dosimeter with a heating piece to thereby heat the dosimeter. The heating steps can in some cases be enhanced by distributing heat using a heat distribution piece or plate, such as plate 85. Although heating is an acceptable means of phosphor stimulation, it is less advantageous than light or optical stimulation. Light stimulation is much faster than heat stimulation and is more easily distributed in a uniform fashion over the surface of a dosimeter. In addition, light stimulation results in quicker release of stored energy, creating more intense luminescence and increasing the signal to noise ratio of the resulting measurements.

The methods further include forming an image using the emission output from the dosimeter sensing area 14 upon stimulation. This image forming or imaging step produces a transitory dosimeter luminescent discharge image from the transitory dosimeter luminescent discharge. Both the luminescent discharge and the resulting discharge image vary from point to point. The discharge varies or is variable across the dose measurement area in relation to the amount of incident radiation beamed onto the dosimetric layer. The derivative discharge image is a nearly identical or close representation of the luminescent discharge from the dose map radiation dosimeter showing the variations in luminescent discharge from location to location across the dosimeter sensing area 14.

The image forming step is accomplished through appropriate optical handling of the luminescent discharge. The preferred imaging step is by appropriately placing the input ends of numerous coherently organized optical fibers near the dosimeter being read. The close placement of the input ends of the optical fibers allows them to collect a large portion of the luminescent discharge, thus improving sensitivity and the signal-to-noise ratio. Close placement of the input ends to the dosimeter also allows improved resolution because the luminescent discharge carried by any one fiber is associated to a greater extent to a limited area of the dosimeter which effectively beams onto that particular fiber. Preferred spacings between the dosimeter and input ends of the optical fibers are less than 10 millimeters, more preferably less than 5 millimeters.

The imaging step can alternatively be performed using a lens (not shown) which is appropriately positioned and oriented to form a focused image onto the image sensor 37.

The preferred system 20 also functions by conveying the transitory luminescent discharge image via the optical fiber bundle 38 to the image sensor 37.

The novel methods of this invention further include sensing the image formed from the transitory dosimeter luminescent discharge across the dose measurement area of the dosimeter. The sensing is preferably performed in a manner which provides a digital pixel by pixel luminescent intensity measurement. This can be accomplished by directing the luminescent discharge image onto a suitable sensor and then prompting the sensor to provide the luminescent discharge information, typically in the form of a digital pixel-specific sensed luminescent output signal. The video camera 36 or other appropriate unit serves by producing digital image data relating to the sensed luminescence intensity. Such digital data might be produced within camera 36, or it may be produced by controller 22 in response to receiving analog signals or data. In general, the digital image data will include a digital value for each element or pixel of image sensor 37. Each such digital value indicates the luminescence intensity of a corresponding region or area of the dose measurement area.

The methods of this invention also preferably include storing the image data. In the embodiment shown, this storing function is advantageously accomplished by data store 28. Other suitable data storage techniques are alternatively possible.

The preferred methods further include analyzing the image data, such as by calculating and deriving a radiation dose map from such digital image data or information. This map deriving process step can be done in a variety of ways to present a clear indication of the dose levels which have been measured by the system. The radiation dose map indicates the energy of the spacially variable radiation pattern across the dose measurement area of the radiation dosimeter.

The methods also preferably include displaying the image information, such as on a computer monitor to an operator or health care provider. This displaying step may include a display of dose map information derived after the analyzing step, or it can otherwise be taken from the image data provided from camera 36.

In the preferred embodiment shown and described, the data processor of computer-based controller 22 is programmed to automate various functions described above. It is connected to receive and store image data from camera 36 and to selectively control and coordinate the operation of stimulator 34. Additional steps affected by controller 22, include analyzing and deriving a dose a map and preferably displaying dose map information to an operator. Data processor 26 can also be programmed to perform more sophisticated analyses of a proposed radiation dose scheme, possibly such as by extrapolating and integrating to this serve in providing a three-dimensional dose map from a plurality of strategically-located dosimeters.

The methods described above improve the process of analyzing and verifying radiation treatment doses. Chemical processing, previously used with X-ray films, is eliminated. Automated test results can be obtained within minutes or seconds, thereby reducing setup times and associated costs. In addition, the novel analysis system is a cost effective alternative to prior technologies.

INDUSTRIAL APPLICABILITY

This invention is applicable to dose mapping of spacially variable radiation patterns, particularly of radiation patterns as are used in the field of medical practice.

I claim:

1. A dose distribution analyzer for providing a digital radiation dose map indicating the strength of a spacially variable radiation pattern beamed onto a dose map radiation dosimeter; the analyzer comprising:

a dose map radiation dosimeter having at least one substantially continuous dose measurement area which is stimulable to emit a transitory dosimeter luminescent discharge image having an intensity which varies across the dose measurement area in relation to the incident strength of a spacially variable radiation pattern previously beamed onto the dose map radiation dosimeter;

a dosimeter holder for holding the dose map radiation dosimeter;

a dosimeter stimulator for emitting a beam of infrared light to stimulate the dose map radiation dosimeter to controllably emit a transitory dosimeter luminescent discharge, said dosimeter stimulator comprising a radiant stimulation beam source which beams a substantially uniform infrared stimulation beam which impinges approximately simultaneously and uniformly across the dosimeter;

a stimulator source filter positioned between the dosimeter stimulator and said dosimeter holder for filtering the stimulating beam which impinges upon the dosimeter;

a coherent bundle of optical fibers positioned to extend from adjacent the dosimeter holder for transferring the transitory dosimeter luminescent discharge image therefrom;

a digital image sensor which is positioned to sense the transitory dosimeter luminescent discharge image transferred by said coherent bundle of optical fibers; said digital image sensor providing digital electronic image information in the form of digital pixel-specific sensed luminescent output values relating to the transitory dosimeter luminescent discharge image sensed by the digital image sensor;

an optical image filter positioned between the dosimeter holder and the digital image sensor to filter the transitory dosimeter luminescent discharge sensed by the digital image sensor;

a data store for storing the digital electronic image information from the digital image sensor which is representative of variable luminescence across the dose map radiation dosimeter to indicate the energy distribution of the spacially variable radiation pattern beamed onto the dose map radiation dosimeter;

a data processor to derive a digital radiation dose map from the digital electronic image information stored by the data store.

2. A dose distribution analyzer according to claim 1 wherein the dosimeter stimulator comprises an incandescent lamp.

3. A dose distribution analyzer according to claim 1 wherein the dosimeter stimulator comprises an incandescent quartz-halogen lamp.

4. A dose distribution analyzer according to claim 1 wherein the dosimeter stimulator comprises an incandescent quartz-tungsten halogen lamp.

5. A dose distribution analyzer according to claim 1 wherein the coherent bundle of optical fibers are tapered optical fibers.

6. A dose distribution analyzer according to claim 1 wherein the data processor includes means for providing a three-dimensional dose map from a plurality of dosimeters.

7. A method of providing a radiation dose map indicating the strength of a spacially variable radiation pattern, the method comprising the following steps:

selecting a dose map radiation dosimeter having at least one substantially continuous dose measurement area which is luminescent and sensitive to variations in the spacially variable radiation pattern;

positioning the dose map radiation dosimeter in a monitoring location within a phantom patient;

exposing the dose map radiation dosimeter positioned in the monitoring location to the spacially variable radiation pattern;

removing the dose map radiation dosimeter from the phantom patient;

positioning the dose map radiation dosimeter previously subjected to the exposing step within a dose distribution analyzer;

beaming a substantially uniform infrared stimulation beam approximately simultaneously across the at least one dose measurement area of the dose map radiation dosimeter to stimulate the at least one dose measurement area to emit a transitory dosimeter luminescent discharge image, said transitory dosimeter luminescent discharge image having luminescence which varies across the at least one dose measurement area in relation to the spacially variable radiation pattern across the at least one dose measurement area;

filtering the infrared stimulation beam to narrow a spectrum beamed onto the at least one dose measurement area;

transferring the transitory dosimeter luminescent discharge image from the dose map radiation dosimeter to a digital image sensor; said transferring including conveying the transitory dosimeter luminescent discharge image within a plurality of optical fibers arranged into a coherent optical fiber array;

sensing the transitory dosimeter luminescent discharge image using the digital image sensor which is capable of providing a digital output with pixel-specific sensed luminescent output values;

storing the pixel-specific sensed luminescent output values in a data store;

deriving a radiation dose map from the pixel-specific sensed luminescent output values, the radiation dose map indicating the spacially variable radiation pattern across the at least one dose measurement area of the dose map radiation dosimeter.

8. A method according to claim 7 wherein said beaming is accomplished using an incandescent lamp.

9. A method according to claim 7 wherein said beaming is accomplished using an incandescent quartz-halogen lamp.

10. A method according to claim 7 wherein said beaming is accomplished using an incandescent quartz-tungsten halogen lamp.

11. A method according to claim 7 further comprising demagnifying the transitory dosimeter luminescent discharge image within a plurality of tapered optical fibers.

12. A method according to claim 7 further comprising analyzing a plurality of dose map radiation dosimeters and producing a three-dimensional dose map therefrom.

* * * * *

UNITED STATES PATENT AND TRADEMARK OFFICE
CERTIFICATE OF CORRECTION

PATENT NO. : 5,661,310
DATED : August 26, 1997
INVENTOR(S) : Scott C. Jones

It is certified that error appears in the above-identified patent and that said Letters Patent is hereby corrected as shown below:

Column 1, line 6, change the word [appliction] to --application--.

Column 3, line 37, delete [incandescent].

Column 7, line 54, after the word "dose", delete the second occurrence of [a].

Column 7, line 58, change the word [this] to --thus--.

Signed and Sealed this

Twentieth Day of January, 1998

Attest:

BRUCE LEHMAN

Attesting Officer

Commissioner of Patents and Trademarks